US010588802B2

(12) United States Patent
Wiggermann et al.

(10) Patent No.: US 10,588,802 B2
(45) Date of Patent: Mar. 17, 2020

(54) SUPPORT SURFACE USEFUL LIFE MONITORING

(71) Applicant: Hill-Rom Services, Inc., Batesville, IN (US)

(72) Inventors: Neal Wiggermann, Batesville, IN (US); Charles A. Lachenbruch, Batesville, IN (US); Timothy J. Receveur, Guilford, IN (US); Joshua A. Williams, West Harrison, IN (US); Rachel L. Williamson, Batesville, IN (US); David L. Bedel, Oldenburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 437 days.

(21) Appl. No.: 15/398,836

(22) Filed: Jan. 5, 2017

(65) Prior Publication Data
US 2017/0196743 A1 Jul. 13, 2017

Related U.S. Application Data

(60) Provisional application No. 62/275,858, filed on Jan. 7, 2016.

(51) Int. Cl.
*A47B 7/02* (2006.01)
*A61G 7/018* (2006.01)
(Continued)

(52) U.S. Cl.
CPC ............. *A61G 7/018* (2013.01); *A61G 7/015* (2013.01); *A61G 7/0506* (2013.01); *A61G 7/057* (2013.01);
(Continued)

(58) Field of Classification Search
CPC .... A61G 7/018; A61G 7/0513; A61G 7/0527; A61G 7/05784; A61G 7/015; A61G 7/0506; A61G 7/057; A61G 7/0573; A61G 2203/34; A61G 2203/16; A61G 2203/20; A61G 2203/36; A61G 2203/42;
(Continued)

(56) References Cited

U.S. PATENT DOCUMENTS 4,179,692 A 12/1979 Vance
4,800,973 A 1/1989 Angel
(Continued)

FOREIGN PATENT DOCUMENTS

JP 2014076256 * 5/2014 ............ A47C 21/00
JP 2014076256 A 5/2014
WO 2012143064 A1 10/2012

OTHER PUBLICATIONS

Machine Translation of the Description of JP2014076256A, 38 pages.
Search Report for EP17150303—1651, 7 pages.

*Primary Examiner* — Nicholas F Polito
*Assistant Examiner* — Morgan J McClure
(74) *Attorney, Agent, or Firm* — Barnes & Thornburg LLP

(57) ABSTRACT

A patient support apparatus includes a frame, a support surface, and a sensor. The frame and the support surface cooperate to support a patient. The sensor is coupled to one of the frame and the support surface and is configured to provide an input signal indicative of usage of the support surface by the patient.

17 Claims, 8 Drawing Sheets

(51) Int. Cl.
*A61G 7/05* (2006.01)
*A61G 7/015* (2006.01)
*A61G 7/057* (2006.01)
*G16H 10/60* (2018.01)
*G16H 50/30* (2018.01)
*G16H 50/70* (2018.01)
*G16H 50/20* (2018.01)

(52) U.S. Cl.
CPC .......... *A61G 7/0513* (2016.11); *A61G 7/0527* (2016.11); *A61G 7/0573* (2013.01); *A61G 7/05784* (2016.11); *G16H 10/60* (2018.01); *G16H 50/30* (2018.01); A61G 2203/16 (2013.01); A61G 2203/20 (2013.01); A61G 2203/34 (2013.01); A61G 2203/36 (2013.01); A61G 2203/42 (2013.01); A61G 2203/44 (2013.01); A61G 2205/60 (2013.01); A61G 2210/70 (2013.01); G16H 50/20 (2018.01); G16H 50/70 (2018.01)

(58) Field of Classification Search
CPC ............ A61G 2203/44; A61G 2203/60; A61G 2203/70; G16H 50/30; G16H 40/60; G16H 40/63; G16H 40/67; G16H 40/40
See application file for complete search history.

(56) References Cited

U.S. PATENT DOCUMENTS

| | | | |
|---|---|---|---|
| 5,253,656 A | 10/1993 | Rincoe et al. | |
| 5,353,012 A | 10/1994 | Barham et al. | |
| 5,515,044 A | 5/1996 | Glatt | |
| 5,808,552 A | 9/1998 | Wiley et al. | |
| 6,067,019 A | 5/2000 | Scott | |
| 6,161,891 A | 12/2000 | Blakesley | |
| 6,208,250 B1 | 3/2001 | Dixon et al. | |
| 7,103,509 B2* | 9/2006 | Shah | G01D 1/00 700/52 |
| 7,107,642 B2 | 9/2006 | Wong et al. | |
| 7,464,605 B2 | 12/2008 | Douglas et al. | |
| 7,752,926 B2 | 7/2010 | Caminade et al. | |
| 8,266,742 B2 | 9/2012 | Andrienko | |
| 8,598,893 B2 | 12/2013 | Camus | |
| 8,717,181 B2 | 5/2014 | Tallent et al. | |
| 8,939,379 B2 | 1/2015 | Myers et al. | |
| 9,005,101 B1 | 4/2015 | Van Erlach | |
| 9,295,600 B2 | 3/2016 | Receveur | |
| 9,358,168 B2 | 6/2016 | Williamson et al. | |
| 9,383,250 B2 | 7/2016 | Receveur et al. | |
| 9,510,784 B2 | 12/2016 | Benson et al. | |
| 9,513,177 B2 | 12/2016 | Shalom et al. | |
| 2002/0080037 A1 | 6/2002 | Dixon et al. | |
| 2003/0029062 A1* | 2/2003 | Esterman | G09F 3/10 40/5 |
| 2005/0278519 A1* | 12/2005 | Luebke | G04F 1/005 713/1 |
| 2006/0271207 A1 | 11/2006 | Shaw | |
| 2007/0089433 A1* | 4/2007 | McDonnell | A23L 3/00 62/115 |
| 2007/0157385 A1 | 7/2007 | Lemire et al. | |
| 2009/0056020 A1 | 3/2009 | Caminade et al. | |
| 2009/0125684 A1* | 5/2009 | Todd | G04F 1/005 711/128 |
| 2010/0011839 A1 | 1/2010 | Browning | |
| 2010/0250448 A1 | 9/2010 | Towe | |
| 2011/0169481 A1 | 7/2011 | Nguyen et al. | |
| 2011/0263950 A1* | 10/2011 | Larson | A61B 5/1113 128/845 |
| 2012/0108215 A1 | 5/2012 | Kameli | |
| 2012/0117730 A1* | 5/2012 | Lemire | A61G 1/0268 5/611 |
| 2012/0259245 A1 | 10/2012 | Receveur | |
| 2013/0021152 A1* | 1/2013 | Vock | A43B 1/0036 340/539.11 |
| 2013/0340500 A1 | 12/2013 | Miller et al. | |
| 2014/0276504 A1 | 9/2014 | Heil et al. | |
| 2014/0333744 A1 | 11/2014 | Baym et al. | |
| 2015/0045630 A1* | 2/2015 | Poliakine-Baruchi | A61B 5/6892 600/301 |
| 2015/0121625 A1* | 5/2015 | Myers | A47C 21/00 5/636 |
| 2016/0136356 A1* | 5/2016 | Ribble | G06F 19/3418 604/111 |
| 2016/0235610 A1 | 8/2016 | Drake | |

\* cited by examiner

SUPPORT SURFACE USEFUL LIFE MONITORING

CROSS-REFERENCE TO RELATED APPLICATIONS

This application claims priority under 35 U.S.C. § 119(e) to U.S. Provisional Application Ser. No. 62/275,858, filed Jan. 7, 2016, which is incorporated herein by reference in its entirety.

BACKGROUND

The present disclosure is related to patient support apparatuses, and in particular to patient support apparatuses including support surfaces subject to degradation during use. More particularly, the present disclosure relates to monitoring the use of support surfaces of patient support apparatuses and mitigating the use of a support surface that has degraded.

Support surfaces wear in response to patient loads being applied to the support surfaces over time. Use of support surfaces beyond their useful lives may degrade the support surfaces and reduce the effectiveness of the support provided by the support surfaces to patients supported thereby. Degradation of the support surfaces may increase the likelihood of skin breakdown and damage of patients supported by the support surfaces.

Support surfaces should be replaced once their useful lives have expired to minimize the likelihood of skin breakdown and damage to patients supported by the support surfaces. By doing so, the substantial costs associated with treating skin breakdown and damage resulting from patient stays on support surfaces in service beyond their useful lives may be avoided. In the past, support surfaces have been replaced based on age, irrespective of use or degradation.

SUMMARY

The present application discloses one or more of the features recited in the appended claims and/or the following features which, alone or in any combination, may comprise patentable subject matter.

According to a first aspect of the present disclosure, a patient support apparatus comprises a frame, support surface, a sensor, and a controller. The frame and a support surface cooperate to support a patient. The sensor is coupled to one of the frame and the support surface. The sensor is configured to provide an input signal indicative of usage of the support surface by the patient. The controller is coupled to the sensor. The controller includes a processor and memory. The controller is configured to receive the input signal and determine whether the support surface should be replaced based on the input signal.

In some embodiments, the input signal is indicative of a compression set of the support surface.

In some embodiments, the patient support apparatus further comprises (i) a RFID tag supported by the support surface and configured to provide a tag signal indicative of the manufacture date of the support surface, and (ii) a RFID reader supported by the frame, coupled to the RFID tag to receive the tag signal, and coupled to the controller to provide the tag signal to the controller.

In some embodiments, the controller is configured to receive the tag signal and determine whether the support surface should be replaced based on the tag signal.

In some embodiments, the controller is configured to determine whether the support surface should be replaced based on a calculated duty cycle of the support surface.

In some embodiments, the duty cycle is adjusted to compensate for one of the weight of the patient supported by the support surface, movement of the patient on the support surface, a compression set of a portion of the support surface, or a position of a head section of a deck of the frame relative to a seat section of the deck.

In some embodiments, the controller is configured to adjust the duty cycle based on the time that a patient is on the support surface.

In some embodiments, the controller is configured to obtain patient information stored in an electronic medical records system that is indicative of a characteristic of the patient and determine whether the support surface should be replaced based on the patient information.

In some embodiments, the characteristic corresponds to a pressure ulcer risk of the patient.

In some embodiments, the controller is configured to obtain patient information provided by the input signal that is indicative of a characteristic of the patient and determine whether the support surface should be replaced based on the patient information.

In some embodiments, the characteristic corresponds to a pressure ulcer risk of the patient.

According to second aspect of the present disclosure, a patient support apparatus comprises a frame, support surface, a sensor, and a controller. The frame and a support surface cooperate to support a patient. The sensor is coupled to one of the frame and the support surface. The sensor configured to provide an input signal indicative of usage of the support surface by the patient. The controller is coupled to the sensor. The sensor includes a processor and memory. The controller is configured to receive the input signal, determine usage of the support surface that has occurred over a predetermined time period based on the input signal, predict usage of the support surface over the predetermined useful life based on the usage determined over the predetermined time period, and determine whether the support surface should be replaced based on the predicted usage.

In some embodiments, the controller is configured to determine usage of the support surface over the predetermined time period based on one of the following: a duty cycle of the support surface, the weight of the patient supported by the support surface, movement of the center of gravity of the patient supported by the support surface, and a position of a head section of a deck of the frame relative to a seat section of the deck.

In some embodiments, the patient support apparatus further comprises (i) a RFID tag supported by the support surface and configured to provide a tag signal indicative of the manufacture date of the support surface and (ii) a RFID reader supported by the frame, coupled to the RFID tag to receive the tag signal, and coupled to the controller to provide the tag signal to the controller.

In some embodiments, the controller is configured to receive the tag signal and determine usage of the support surface that has occurred over the predetermined time period based on the tag signal.

In some embodiments, the predetermined time period begins from the manufacture date of the support surface indicated by the tag signal.

According to a third aspect of the present disclosure, a method of operating a patient support apparatus including a frame, a support surface, and a sensor configured to provide an input signal indicative of usage of the support surface by a patient, the method comprises receiving the input signal, and determining whether the support surface should be replaced based on the input signal.

In some embodiments, the input signal is indicative of a compression set of the support surface.

In some embodiments, the controller is configured to determine whether the support surface should be replaced based on one of the following: a duty cycle of the support surface, the weight of the patient supported by the support surface, the center of gravity of the patient supported by the support surface, and a position of a head section of a deck of the frame relative to a seat section of the deck.

In some embodiments, the method further comprises predicting usage of the support surface over a predetermined useful life of the support surface based on the input signal, wherein determining whether the support surface should be replaced based on the input signal comprises determining whether the support surface should be replaced based on the predicted usage.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
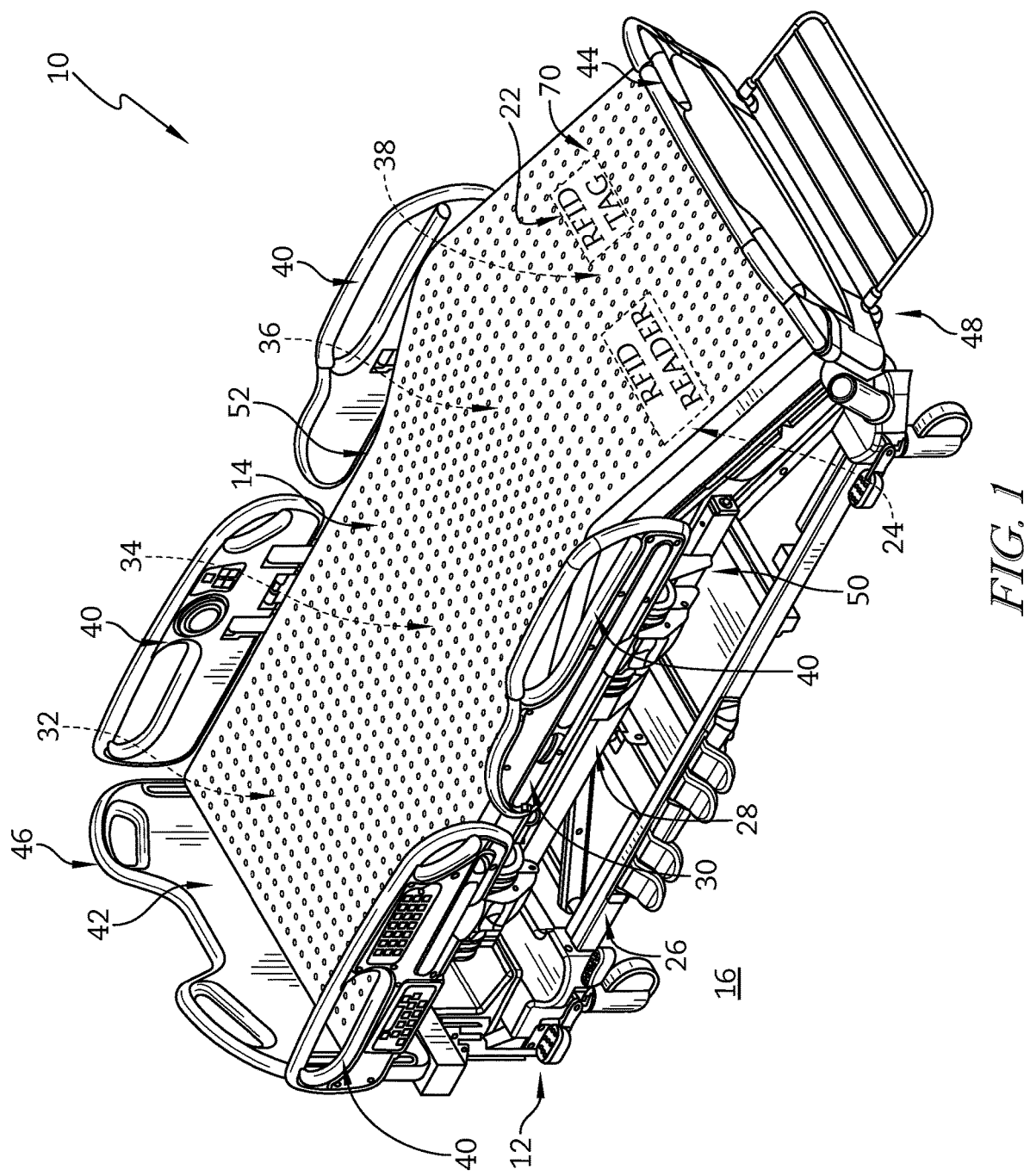
FIG. 1 is a perspective view of a patient support apparatus that includes a frame, a support surface cooperating with the frame to support a patient (omitted for the sake of simplicity), a RFID tag supported by the support surface, and a RFID reader supported by the frame.

Referring to FIG. 1, an illustrative patient support apparatus 10 is shown. The patient support apparatus 10 includes a frame 12 supported by wheels or casters and a support surface 14 that cooperates with the frame 12 to support a patient above a floor 16 on which the patient support apparatus 10 rests.

Figure 3:
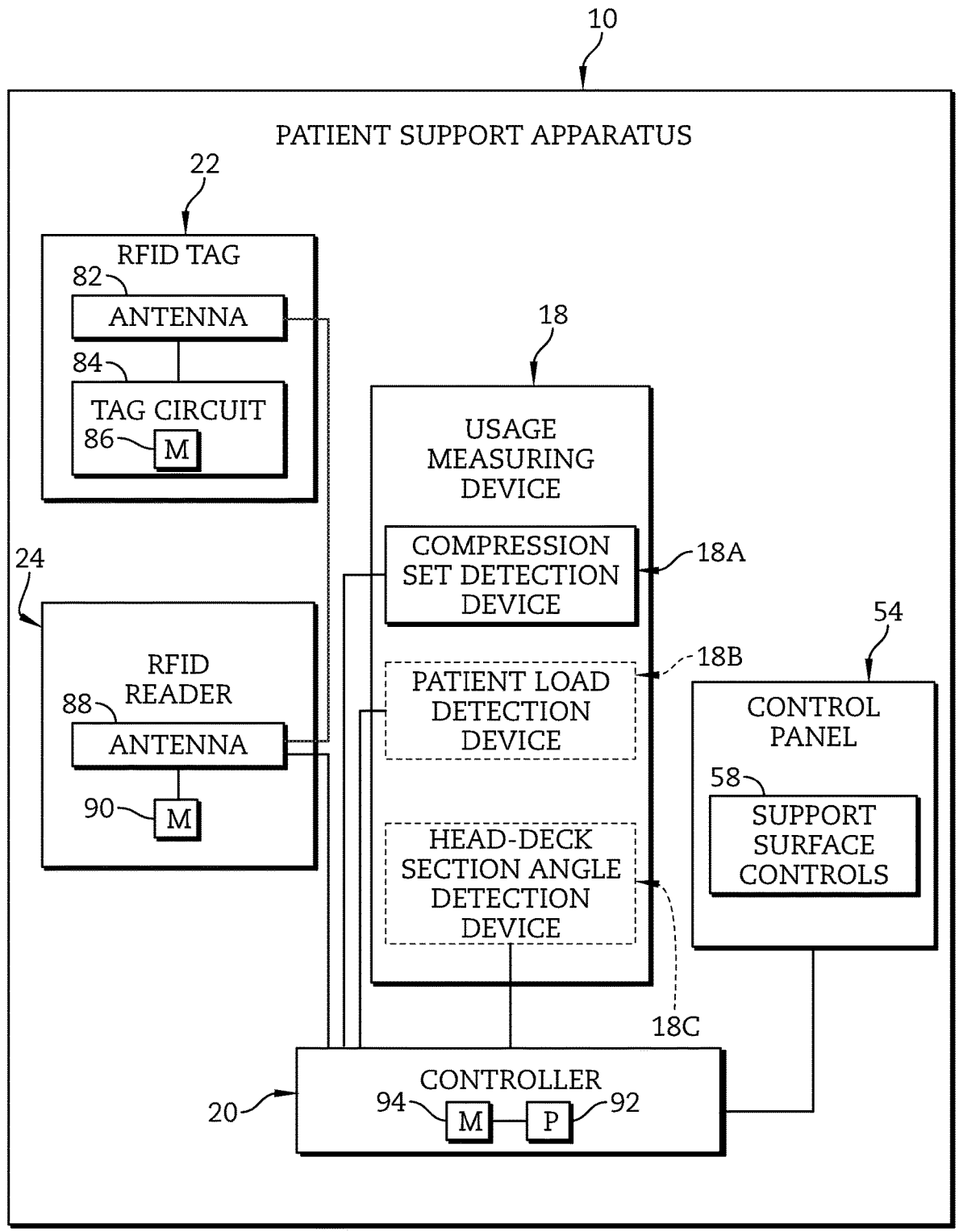
FIG. 3 is a diagrammatic view of the patient support apparatus of FIG. 1 showing components included in and interrelationships between the RFID tag, the RFID reader, the controller, the usage measuring device, and the control panel.

Referring to FIG. 3, the patient support apparatus 10 further includes a usage measuring device or sensor 18 that is coupled to one of the frame 12 and the support surface 14. The sensor 18 is configured to provide an input signal indicative of usage of the support surface 14 by the patient. As will be explained in further detail below, the usage measuring device 18 may include a single sensor or multiple sensors, with each sensor providing different information used to determine the usage parameters of the support surface 14. The patient support apparatus 10 further includes a controller 20 that is coupled to the sensor 18 and supported by the frame 12. The controller 20 is configured to receive the input signal and determine whether the support surface 14 should be replaced based on the input signal.

Usage of the support surface 14 by the patient is illustratively characterized by the detected presence, or lack thereof, of the patient on the support surface 14 over time. The sensor 18 is therefore illustratively embodied as, or otherwise includes, one or more devices configured to monitor the presence (or absence) of the patient on the support surface 14 over time as discussed below. The sensor 18 may also be referred to herein as a usage measuring device.

In some embodiments, the controller 20 may be configured to determine usage of the support surface 14 by the patient without predicting usage of the support surface 14 based on the input signal provided by the sensor 18. In such embodiments, the controller 20 may be configured to determine whether the support surface 14 should be replaced without predicting usage of the support surface 14. In other embodiments, the controller 20 may be configured to predict usage of the support surface 14 based on the input signal provided by the sensor 18. In such embodiments, the controller 20 may be configured to determine whether the support surface 14 should be replaced based on the predicted usage of the support surface 14.

The patient support apparatus 10 shown in FIG. 1 is illustratively embodied as a hospital bed. In other embodiments, however, the patient support apparatus 10 may be embodied as any one of a number of suitable patient support apparatuses. For example, the patient support apparatus 10 may be embodied as a recovery bed, a wheel chair, a stretcher, or the like.

Figure 2:
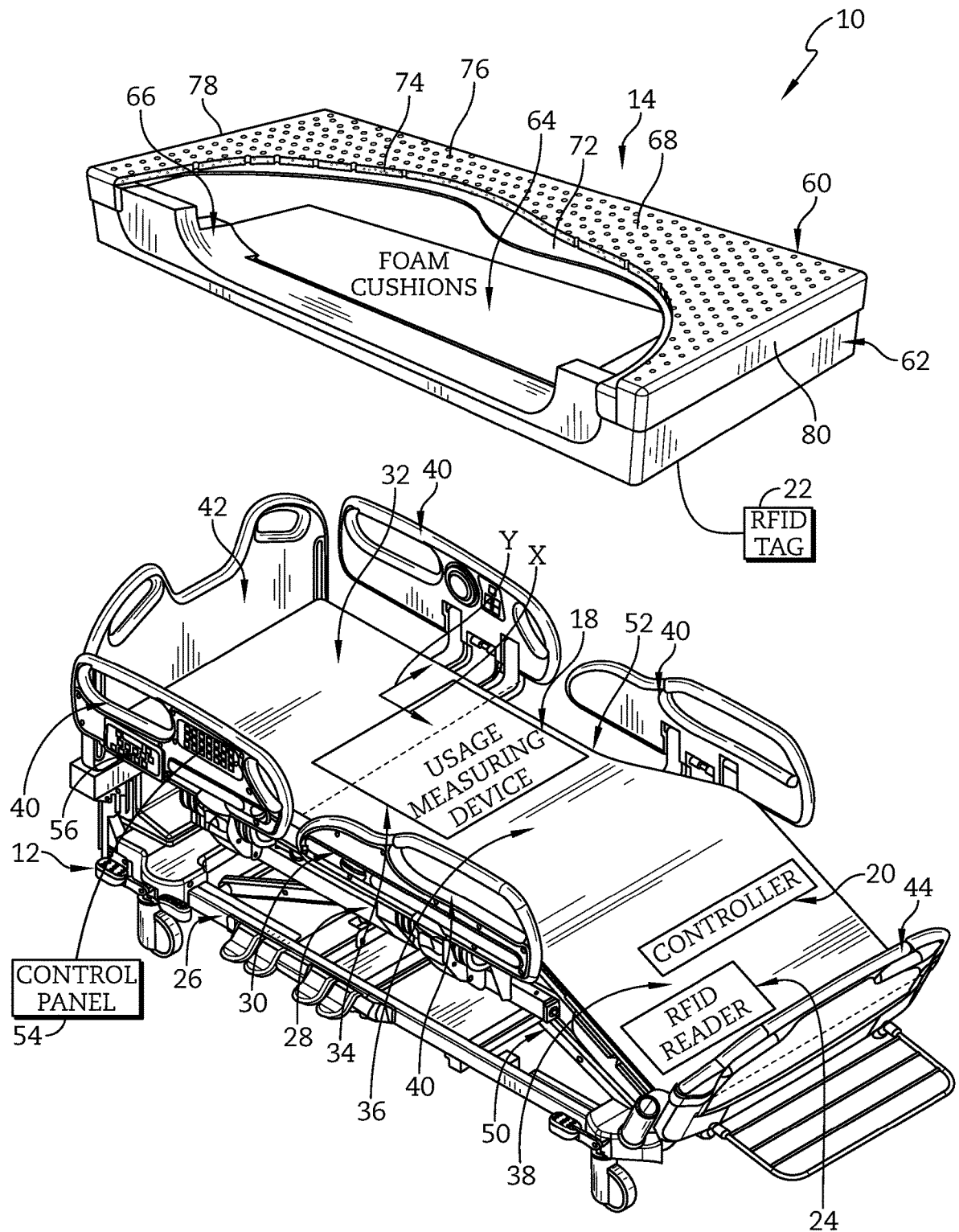
FIG. 2 is an exploded assembly view of the patient support apparatus of FIG. 1 showing that the RFID tag is coupled to an exterior surface of the support surface and, wherein the support surface includes foam cushions, and that the patient support apparatus includes a controller, a control panel, an RFID reader, and a usage measuring device supported by the frame.

The patient support apparatus 10 illustratively includes a RFID tag 22 and a RFID reader 24, each of which are shown in simplified diagrammatic form in FIG. 1. The RFID tag 22 is supported by the support surface 14 as best seen in FIG. 2. The RFID tag 22 is configured to provide a tag signal indicative of information specific to the support surface 14, such as a serial number and manufacture date of the support surface 14 as discussed below. The RFID reader 24 is electrically coupled to the controller 20 to receive the tag signal from the RFID tag 22 and provide the tag signal to the controller 20 as discussed below.

Referring now to FIG. 2, the illustrative frame 12 of the patient support apparatus 10 is shown in detail. The frame 12 includes a lower frame 26, an upper frame 28, and a deck 30 coupled to the upper frame 28. The deck 30 is movable to a plurality of positions as suggested by FIG. 2. The deck 30 includes a head-deck section 32, a seat-deck section 34, a thigh-deck section 36, and a foot-deck section 38. The head-deck section 32 is mounted to the upper frame 28 to pivot about an axis relative to the seat-deck section 34 and to slide relative to the seat-deck section 34 and the upper frame 28 as described U.S. Publication Nos. 2010/0122415 and 2012/0005832, each of which is incorporated herein in their entirety. The seat-deck section 34 is coupled to the upper frame 28 to move with the upper frame 28. The thigh-deck section 36 is coupled to the seat-deck section 34 to pivot relative to the seat-deck section 34. The foot-deck section 38 is coupled to the thigh-deck section 36 to pivot relative to the thigh-deck section 36. The foot-deck section 38 is also extendable and retractable to lengthen or shorten the deck 30 as desired by a caregiver or to accommodate repositioning of the deck 30.

The patient support apparatus 10 illustratively includes a number of siderails 40, a headboard 42, and a footboard 44, each of which is supported by the frame 12 as shown in FIG. 2. The headboard 42 is positioned adjacent a head end 46 of the patient support apparatus 10. The footboard 44 is positioned adjacent a foot end 48 of the patient support apparatus 10 arranged opposite the head end 46. The siderails 40 extend between the head and foot ends 46, 48 along opposite sides 50, 52 of the patient support apparatus 10.

The patient support apparatus 10 illustratively includes a control panel 54 as shown in FIG. 2. The control panel 54 embodies a caregiver input-output device that is coupled to the controller 20 to communicate with the controller 20. In the illustrative embodiment, the control panel 54 is affixed to one of the siderails 40 and is thereby supported by the frame 12. In other embodiments, however, the control panel 54 may be affixed to another component of the patient support apparatus 10 so that the control panel 54 is supported by the frame 12. In other embodiments still, the control panel 54 may be removably coupled to the frame 12.

The control panel 54 illustratively includes a touchscreen display 56 as shown in FIG. 2. The touchscreen display 56 provides a user interface enabling the caregiver to configure, activate, and deactivate certain electronically controlled functions of the patient support apparatus 10. The display 56 may provide visual indications to the caregiver regarding certain of the electronically controlled functions of the patient support apparatus 10 or certain characteristics of the patient. The control panel 54 may also include a speaker configured to provide audible indications to the patient or the caregiver.

In addition to the control panel 54, the patient support apparatus 10 may further include other caregiver input-output devices capable of receiving and processing electrical input from a number of manually operable switches coupled to the caregiver input-output devices. The caregiver input-output devices may enable the caregiver to configure, activate, and deactivate certain of the electronically controlled functions of the patient support apparatus 10.

The patient support apparatus 10 may further include patient input-output devices capable of receiving and processing electrical input from a number of manually operable switches coupled to the patient input-output devices. The patient input-output devices may be used to enable the patient to activate and deactivate certain electronically controlled functions of the patient support apparatus 10 when the patient is positioned on the support surface 14.

The usage measuring device 18 (shown in simplified diagrammatic form) illustratively includes as a device or system configured to measure the degree to which the support surface 14 is permanently deformed when a load (e.g., a patient load) applied to the support surface 14 is removed (e.g., when the patient exits the support surface 14). For instance, the usage measuring device 18 may include electrical contacts or another suitable sensing device configured to measure the compression set of the support surface 14, such as the compression set detection device 18A shown in FIG. 3. While the compression set detection device 18A is shown in solid lines in FIG. 3, it should be understood that the compression set detection device 18A may be omitted in some embodiments and other sensors may be utilized for the usage measuring device 18.

In some embodiments, the usage measuring device 18 may further include a device or system configured to detect the patient's weight, or lack thereof, on the support surface 14 as suggested by FIG. 2. The usage measuring device 18 may include one or more load cells configured to detect a patient load applied by the patient to the support surface 14, such as the patient load detection device 18B shown in phantom in FIG. 3. The usage measuring device 18 may also be embodied as, or otherwise include, a patient positioning monitoring system.

In some embodiments, the usage measuring device 18 may further include a device or system configured to measure the angle of the head-deck section 32 relative to the seat-deck section 34. The usage measuring device 18 may include one or more potentiometers or accelerometers configured to measure the angle of the head-deck section 32 relative to the seat-deck section 34, such as the head-deck section angle detection device 18C shown in phantom in FIG. 3.

In some embodiments, the patient load detection device 18B may be used to determine the patient's center of gravity on the support surface 14. Based on the patient load indicated by the device 18B to be applied to the support surface 14, the controller 20 may determine the location of a centroid of the patient load (i.e., the patient's center of gravity) and thus the position of the patient on the support surface 14. The location of the centroid of the patient load may be represented by a coordinate (X, Y) within a two-dimensional Cartesian coordinate system in which axes X and Y are defined along the support surface 14. The controller 20 may be configured to determine whether the support surface 14 should be replaced based on the patient's center of gravity as discussed below.

In some embodiments, the determination of the patient's center of gravity may be affected by the angle of the head-deck section 32 relative to the seat-deck section 34 indicated by the head-deck section angle detection device 18C. As such, the controller 20 may be configured to determine whether the support surface 14 should be replaced based on the angle of the head-deck section 32 relative to the seat-deck section 34 indicated by the device 18C.

In some embodiments, the patient load detection device 18B may be used to determine movement of the patient on the support surface 14. Based on the patient load indicated by the device 18B to be applied to the support surface 14, the controller 20 may calculate the rate of change in patient load on the support surface 14 over time to determine movement of the patient on the support surface 14. The controller 20 may be configured to determine whether the support surface 14 should be replaced based on movement of the patient on the support surface 14 as discussed below.

In some embodiments, the patient load detection device 18B may be used to determine one or more duty cycles of the support surface 14. When the patient load is indicated by the device 18B to be applied to the support surface 14, the controller 20 may initialize a timer to track the time period during which the support surface 14 is in use by the patient (i.e., the duty cycle of the support surface 14). The controller 20 may be configured to determine whether the support surface 14 should be replaced based on the one or more duty cycles of the support surface 14 as discussed below. The duty cycle may include the total amount of time that the load is applied. In some embodiments, the duty cycle may further factor in the patient's weight into the duty cycle calculation. For example a patient weighing 200 pounds will tend to degrade a support surface 14 to a greater extent than a patient weighing 150 pounds, for the same time period of use. The higher load will tend to degrade the components of the support surface 14. Thus, it is contemplated that the duty cycle calculation may, in some embodiments, accumulate the load as a function of time to determine the duty cycle.

The support surface 14 is illustratively embodied as, or otherwise includes, a deformable support surface such as a mattress as shown in FIG. 2. The support surface 14 includes a topper 60 and a lower ticking 62 that cooperate to encase a plurality of foam cushions 64 (shown in simplified diagrammatic form) and a foam shell 66. The topper 60 forms a top face 68 of the support surface 14. The topper 60 may be configured to conduct pressurized air along an interface between the patient and the support surface 14 to cool and dry the patient's skin when the patient is supported on the support surface 14. In some embodiments, the support surface 14 may also include a coverlet 70 encasing the topper 60 and the lower ticking 62.

In the illustrative embodiment, the foam cushions 64 and the foam shell 66 have a polymeric construction. For example, the foam cushions 64 and the foam shell 66 are constructed of latex, viscoelastic, or polyurethane materials. It should be appreciated, however, that in other embodiments, the foam cushions 64 and the foam shell 66 may have another suitable construction.

In the illustrative embodiment, the foam cushions 64 cooperate to support the patient supported on the support surface 14. Patient usage of the support surface 14 causes the foam cushions 64 to wear over time, thereby reducing cushioning and support provided by the foam cushions 64. The useful life of the support surface 14 as described herein therefore refers primarily to the useful life of the foam cushions 64 (i.e., the predetermined period during which cushioning and support provided by the foam cushions 64 is deemed to be acceptable). As such, the controller 20 is configured to determine whether the support surface 14 should be replaced based primarily on whether the useful life of the foam cushions 64 has been exceeded.

In other embodiments, however, the foam cushions 64 may cooperate with other components to support the patient supported on the support surface 14. For example, the foam cushions 64 may cooperate with polyurethane gels and/or inflatable air bladders to support the patient supported on the support surface 14. In those embodiments, the controller 20 may be configured to determine whether the support surface 14 should be replaced based at least in part on whether the useful life of the polyurethane gels and/or the inflatable air bladders has been exceeded.

The topper 60 illustratively includes a bottom layer 72, a middle layer 74, and a top layer 76 as shown in FIG. 2. The middle layer 74 may be a three-dimensional material that allows pressurized air to flow between the bottom layer 72 and the top layer 76 along the top face 66 between opposite head and foot ends 78, 80 of the support surface 14. The top layer 76 may be made from a perforated material that allows moisture from the patient supported on the support surface 14 to pass through the top layer 76 and be carried away for evaporation by air flowing through the middle layer 74. For example, the top layer 76 may be made from, or otherwise include, a urethane coated nylon ticking material that is air impermeable but vapor permeable.

In other embodiments, air-flow cooled toppers other than the topper 60 may be used with the support surface 14. For example, air-loss toppers, air-fluidized bead toppers, and the like may be used with the support surface 14.

The RFID tag 22 is illustratively attached to the top face 68 of the support surface 14 as shown in FIG. 2. The RFID reader 24 is illustratively positioned within the support surface 14 for communication with the RFID tag 22. Specifically, the RFID reader 24 is positioned within the support surface 14 in sufficient proximity to the RFID tag 22 to permit communication between the RFID reader 24 and the RFID tag 22. It should be appreciated, however, that in other embodiments, the RFID tag 22 may be attached to another surface of the support surface 14. In that case, as indicated above, the RFID reader 24 should be positioned within the support surface 14 in sufficient proximity to the RFID tag 22 to permit communication between the RFID reader 24 and the RFID tag 22.

Referring now to FIG. 3, components included in each of the RFID tag 22, the RFID reader 24, the usage measuring device 18, the controller 20, and the control panel 54 are shown in detail. The RFID tag 22 is coupled to the RFID reader 24, and the RFID reader 24 is coupled to the controller 20 as indicated above. Each of the usage measuring device 18 and the control panel 54 are coupled to the controller 20 as indicated above.

The RFID tag 22 illustratively includes a tag antenna 82 as shown in FIG. 3. The tag antenna 82 is configured to receive an incoming radio frequency signal provided to the RFID tag 22 by the RFID reader 24 so that information may be communicated from the RFID reader 24 to the RFID tag 22. Additionally, the tag antenna 82 is configured to transmit an outgoing radio frequency signal to the RFID reader 24 so that information may be communicated from the RFID tag 22 to the RFID reader 24.

The RFID tag 22 further illustratively includes a tag circuit 84 that is coupled to the tag antenna 82 as shown in FIG. 3. The tag circuit 84 is embodied as, or otherwise includes, an integrated circuit having tag memory 86. Tag memory 86 is configured to store information which may be used to identify the support surface 14 to which the RFID tag 22 is attached. In the illustrative embodiment, tag memory 86 stores the manufacture date and the serial number of the support surface 14, and that information may be transmitted in the form of the tag signal from the tag antenna 82 to the RFID reader 24. Tag memory 86 may be embodied as, or otherwise include, one or memory devices or data storage locations including, for example, dynamic random access memory devices (DRAM), synchronous dynamic random access memory devices (SDRAM), double-data rate synchronous dynamic random access memory device (DDR SDRAM), mask read-only memory (ROM) devices, erasable programmable ROM (EPROM), electrically erasable programmable ROM (EEPROM) devices, flash memory devices, and/or other volatile and/or non-volatile memory devices. In some embodiments, the tag circuit 84 may include a tag processor that is configured to perform any number of activities according to instructions stored in tag memory 86. For example, the tag processor may be configured to modulate and demodulate the signal provided to the tag antenna 82 by the RFID reader 24 according to instructions stored in tag memory 86. The tag processor may be embodied as, or otherwise include, one or more microprocessors, digital signal processors, microcontrollers, discrete circuitry, and/or the like.

In the illustrative embodiment, the RFID tag 22 is a passive tag that does not include a power source and is powered by the incoming radio frequency signal provided to the RFID tag 22 by the RFID reader 24. It should be appreciated, however, that in other embodiments, the RFID tag 22 may be an active or battery-assisted passive RFID tag.

The RFID reader 24 illustratively includes a reader antenna 88 as shown in FIG. 3. The reader antenna 88 is coupled to the tag antenna 82 and is configured to provide the incoming radio frequency signal to the tag antenna 82. Additionally, the reader antenna 88 is configured to receive the outgoing radio frequency signal from the tag antenna 82, which may be in the form of the tag signal as indicated above. The reader antenna 88 is also coupled to the controller 20 by communication circuitry included in the patient support apparatus 10. For example, the reader antenna 88 may be coupled to the controller 20 by Bluetooth circuitry included in the patient support apparatus 10.

The RFID reader 24 further illustratively includes reader memory 90 that is coupled to the reader antenna 88 as shown in FIG. 3. Reader memory 90 is configured to store information indicative of usage of the support surface 14 by the patient detected by the usage measuring device 18 as discussed below. Reader memory 90 may be embodied as, or otherwise include, one or memory devices or data storage locations including, for example, dynamic random access memory devices (DRAM), synchronous dynamic random access memory devices (SDRAM), double-data rate synchronous dynamic random access memory device (DDR SDRAM), mask read-only memory (ROM) devices, erasable programmable ROM (EPROM), electrically erasable programmable ROM (EEPROM) devices, flash memory devices, and/or other volatile and/or non-volatile memory devices.

In some embodiments, the RFID reader 24 may include a reader processor that is configured to perform any number of activities according to instructions stored in reader memory 90. For example, the reader processor may be configured to direct the RFID reader 24 to receive information indicative of usage of the support surface 14 detected by the usage measuring device 18 from the controller 20 according to instructions stored in reader memory 90. The reader processor may be embodied as, or otherwise include, one or more microprocessors, digital signal processors, microcontrollers, discrete circuitry, and/or the like.

The usage measuring device 18 illustratively includes the compression set detection device 18A, the patient load detection device 18B, and the head-deck section angle detection device 18C as shown in FIG. 3 and indicated above. The device 18A is coupled to the controller 20 to provide input thereto indicative of the compression set of the support surface 14. The device 18B is coupled to the controller 20 to provide input thereto indicative of the patient load applied to the support surface 14. The device 18C is coupled to the controller 20 to provide input thereto indicative of the angle of the head-deck section 32 relative to the seat-deck section 34.

The control panel 54 illustratively includes support surface controls 58 as shown in FIG. 3. The controls 58 enable the caregiver to configure, activate, and deactivate certain of the electronically controlled functions of the support surface 14. In response to the determination that the support surface 14 should be replaced, certain of the controls 58 may be disabled or enabled as discussed below.

The illustrative controller 20 manages a variety of electronically controlled functions associated with the patient support apparatus 10. The controller 20 includes a controller processor 92 and controller memory 94 coupled to the controller processor 92. The memory 94 includes instructions that are executable by the processor 92 to cause the processor 92 to perform a variety of activities, as discussed below with reference to FIGS. 5-8. Memory 94 may be embodied as, or otherwise include, one or memory devices or data storage locations including, for example, dynamic random access memory devices (DRAM), synchronous dynamic random access memory devices (SDRAM), double-data rate synchronous dynamic random access memory device (DDR SDRAM), mask read-only memory (ROM) devices, erasable programmable ROM (EPROM), electrically erasable programmable ROM (EEPROM) devices, flash memory devices, and/or other volatile and/or non-volatile memory devices. The processor 92 may be embodied as, or otherwise include, one or more microprocessors, digital signal processors, microcontrollers, discrete circuitry, and/or the like.

Figure 4:
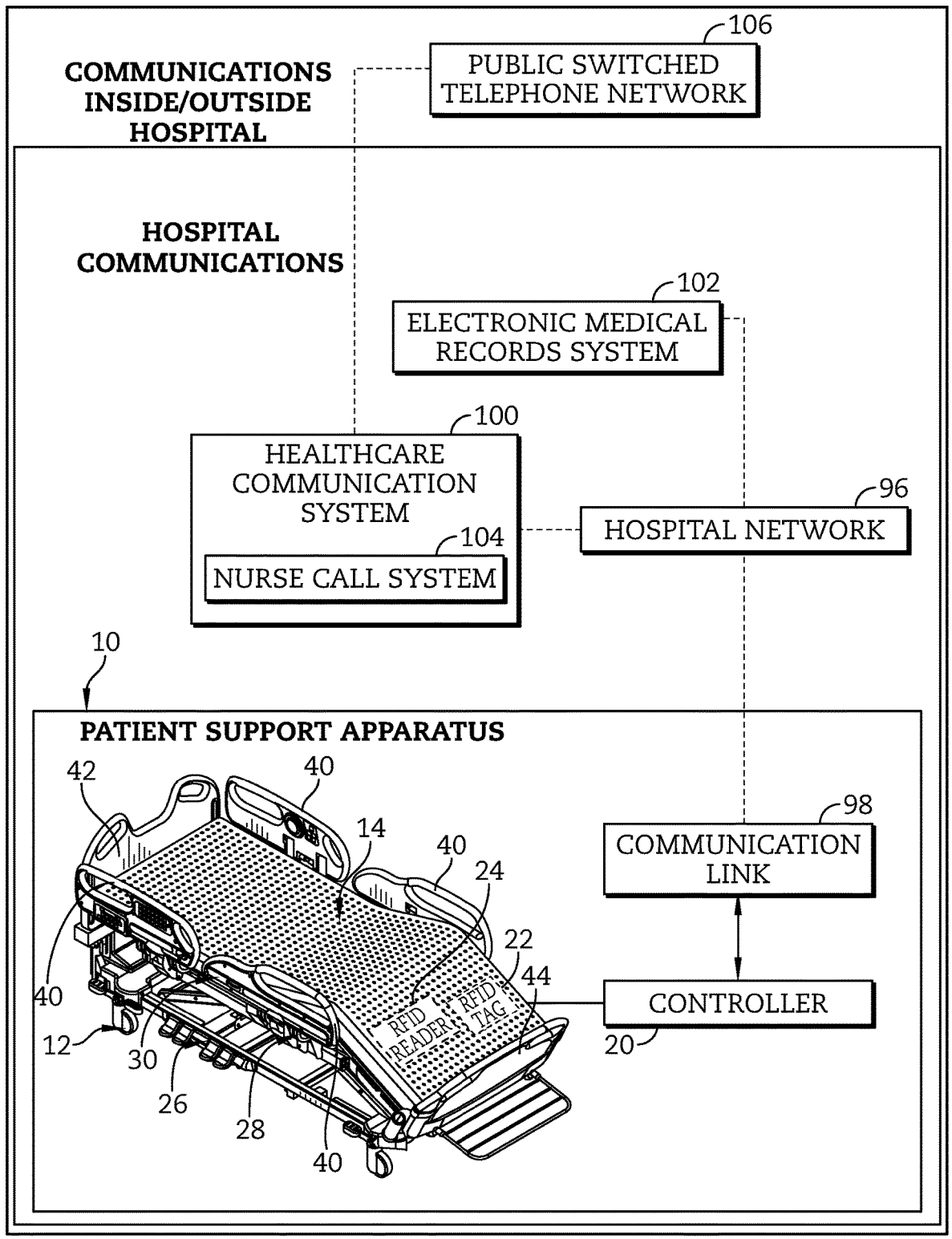
FIG. 4 is a diagrammatic view of the patient support apparatus of FIG. 1 showing a communication path between the controller and an electronic medical records system and between the controller, a healthcare communication system including a nurse call system, and a public switched telephone network.

Communication paths between the patient support apparatus 10 and systems/networks located inside the hospital in which the patient support apparatus 10 is located and between the patient support apparatus 10 and system/networks located outside the hospital are shown in FIG. 4. The patient support apparatus 10, specifically the controller 20, is illustratively coupled to a hospital network 96 through a communication link 98. The communication link 98 enables electrical communications originating at the patient support apparatus 10 (e.g., at the controller 20) to be communicated to the hospital network 96. In one example, the communication link 98 may be a wireless device enabling data to be exchanged between the controller 20 and the hospital network 96, such as a Bluetooth device. In another example, the communication link 98 may be a wired RS-232 connection permitting data to be exchanged between the controller 20 and the hospital network 96.

The hospital network 96 illustratively couples the controller 20 to a healthcare communication system 100 and to an electronic medical records system 102 of the hospital as shown in FIG. 4. The hospital network 96 may be embodied as, or otherwise include, a local area network, a wide area network, a secure enterprise cloud, secure portions of the Internet, and/or others. In some embodiments, in addition to the hospital network 96, intermediate devices and/or circuitry may enable the controller 20 to interface with the healthcare communication system 100 and with the electronic medical records system 102. For example, an input-output (I/O) board and a switch (e.g., a Power over Ethernet (POE) switch) may be used to communicatively couple the controller 20 to the healthcare communication system 100 and to the electronic medical records system 102.

The electronic medical records system 102 is illustratively used to store data for patients receiving care at the hospital as suggested by FIG. 4. Patient information such as the patient's name, data indicating the patient's pressure ulcer risk according to a standardized scale such as the Braden scale, and patient movement data on the support surface 14 detected by the usage measuring device 18, among other things, may be stored in an electronic history file (EHF) in a database included in the electronic medical records system 102. Additionally, information particular to the support surface 14 may be stored in the electronic medical records system 102. For example, the manufacture date and serial number of the support surface 14 stored in the RFID tag 22, as well as usage of the support surface 14 monitored by the usage measuring device 18, may be stored in a database included in the electronic medical records system 102.

The healthcare communication system 100 illustratively includes a nurse call system 104 which may include a master station and a number of user stations. Each of the nurse call system 104 user stations may include computers permitting caregiver access to patient information and information particular to the support surface 14 stored in the electronic medical records system 102. The nurse call system 104 may also utilize server computers provided at the master station or the user stations to operate and manage certain functions of the nurse call system 104. For example, the server computers may receive and manage communications from devices connected to the nurse call system, control the placement, cancelling, and answering of nurse calls, and generate notifications/alerts prompting caregivers to assist patients.

The healthcare communication system 100 is coupled to a telecommunications server which acts as a gateway to the hospital's telecommunications infrastructure. The hospital's telecommunications infrastructure illustratively includes a network 106 that facilitates communication among a variety of telecommunication devices, including analog and digital devices, fixed telephones or mobile or cellular devices carried by hospital personnel, personal data assistants (PDAs), pagers, and the like.

In the illustrative embodiment, the network 106 is embodied as, or otherwise includes, a public switched telephone network (PTSN) as shown in FIG. 4. In other embodiments, however, the network 106 may be embodied as, or otherwise include, other suitable networks, such as a private branch exchange (PBX), or the like. The public switched telephone network 106 may be used to transmit communications originating at the patient support apparatus 10 (i.e., at the controller 20), or at another location inside the hospital, to one or more devices held by persons concerned with replacement of the support surface 14 who are located inside or outside of the hospital.

Figure 5:
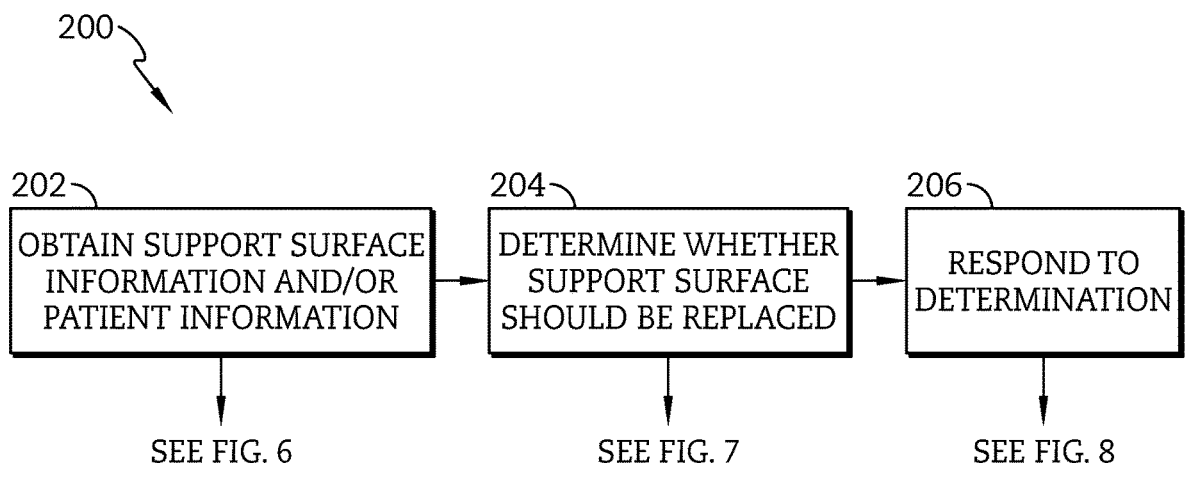
FIG. 5 is a diagrammatic view of a process executable by the controller of FIG. 4 to operate the patient support apparatus.

Referring now to FIG. 5, an illustrative process 200 executable by the controller 20 (i.e., the controller processor 92) to operate the patient support apparatus 10 is shown. The process 200 defines a sequence of steps for operating the patient support apparatus 10 that are stored in controller memory 94. The process 200 begins at a step 202 which directs the controller 20 to obtain information regarding the support surface 14 and/or information regarding the patient supported on the support surface 14, as discussed below with reference to FIG. 6. The process 200 proceeds to a step 204 which directs the controller 20 to determine whether the support surface 14 should be replaced, as discussed below with reference to FIG. 7. The process 200 concludes with a step 206 which directs the controller 20 to respond to the determination made in step 204, as discussed below with reference to FIG. 8.

Figure 6:
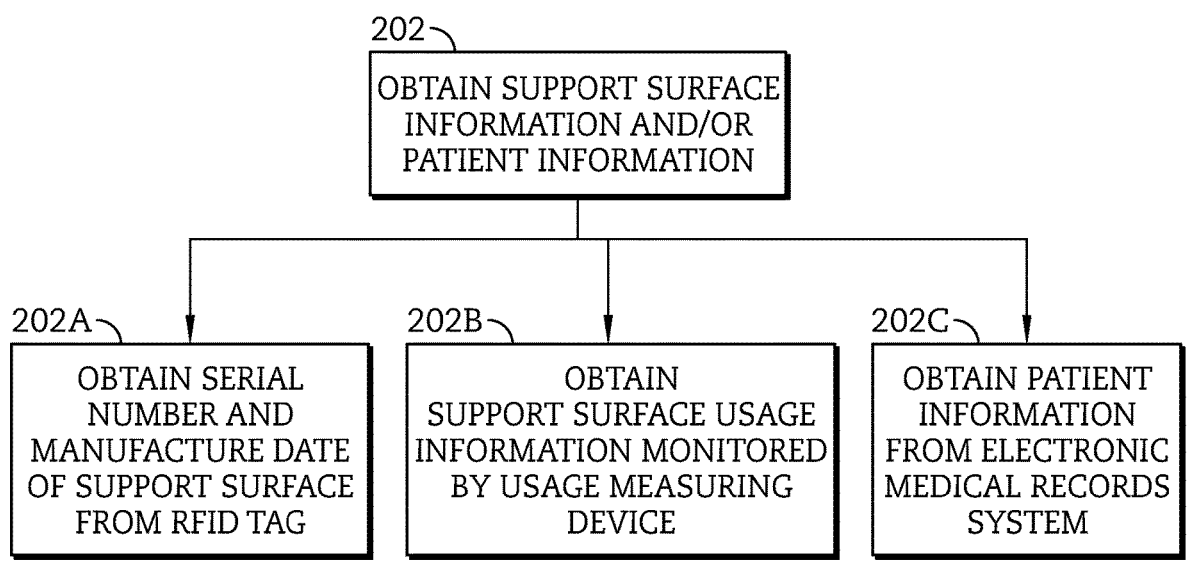
FIGS. 6-8 are diagrammatic views of activities included in the process of FIG. 5.

Referring now to FIG. 6, the step 202 of the process 200 is shown in detail. The step 202 includes sub-steps 202A, 202B, and 202C. In the illustrative embodiment, the controller 20 executes at least one of the sub-steps 202A, 202B, or 202C to execute the step 202. It should be appreciated, however, that in other embodiments, the controller 20 may execute two or more of the sub-steps 202A, 202B, and 202C to execute the step 202. In those embodiments, the two or more of the sub-steps 202A, 202B, and 202C may be executed by the controller 20 successively (i.e., one after the other) or contemporaneously (i.e., at the same time). Each of the sub-steps 202A, 202B, and 202C are described below.

The controller 20 may execute the step 202 by executing the sub-step 202A as indicated above. The sub-step 202A illustratively directs the controller 20 to obtain the serial number and manufacture date of the support surface 14 from the RFID tag 22 as shown in FIG. 6. The serial number and manufacture date of the support surface 14 may define or be associated with the predetermined useful life of the support surface 14. As such, the predetermined useful life of the support surface 14 may be obtained from the RFID tag 22 by the controller 20 during execution of the sub-step 202A. Additionally, the serial number and manufacture date of the support surface 14 may also define or be associated with a predetermined replacement compression set of the support surface 14. The predetermined replacement compression set of the support surface 14 may therefore be obtained from the RFID tag 22 by the controller 20 during execution of the sub-step 202A.

The controller may execute the step 202 by executing the sub-step 202B as indicated above. Sub-step 202B illustratively directs the controller 20 to obtain usage information regarding usage of the support surface 14 that is monitored by the usage measuring device 18 when the support surface 14 is in use. It should be appreciated that the usage information monitored by the usage measuring device 18 and obtained during execution of the sub-step 202B may describe usage of the support surface 14 by any number of patients while the support surface 14 is in use. The support surface 14 is in use during a predetermined time period that begins from either the manufacture date of the support surface 14 or the earliest date that information stored in the tag memory 86 is communicated to the controller 22 and ends when the process 200 is executed. The support surface 14 is also in use after the predetermined time period has elapsed. It should also be appreciated that usage information obtained during the sub-step 202B may be indicative of one or more of the following accumulated while the support surface 14 is in use: the compression set(s) of the support surface 14, the load(s) applied to the support surface 14, the angle(s) of the head-deck section 32 relative to the seat-deck section 34, patient center(s) of gravity on the support surface 14, patient movement(s) on the support surface 14, and the duty cycle(s) of the support surface 14. The duty cycle of the support surface 14 may include a time factor and a load factor. In addition, the duty cycle of the support surface 14 also is adjusted to compensate for the angle of the head deck-section 32, the movement of the patient on the support surface 14, or existing compression set of the support surface 14.

In the illustrative embodiment, usage information monitored by the usage measuring device 18 while the support surface 14 is in use is stored in reader memory 90 after being communicated initially to the controller 20 (i.e., in the form of the input signal) and prior to being obtained by the controller 20 during execution of the sub-step 202B. It should be appreciated, however, that in other embodiments, usage information monitored by the usage measuring device 18 while the support surface 14 is in use may be stored in another suitable location, such as tag memory 86 or the electronic medical records system 102. Each of these storage locations permits the usage information to be updated over the predetermined useful life of the support surface 14 to reflect usage of the support surface 14 in multiple patient support apparatuses under a variety of circumstances.

The controller 20 may execute the step 202 by executing the sub-step 202C as indicated above. The sub-step 202C illustratively directs the controller 20 to obtain patient information from the electronic medical records system 102 as shown in FIG. 6. In the illustrative embodiment, patient information obtained by the controller 20 during execution of the sub-step 202C corresponds to at least one of the following contained in electronic history files: patient pressure ulcer risk according to the Braden scale or patient pressure ulcer risk according to patient movements detected on the support surface 14 by the usage measuring device 18 while the support surface 14 is in use.

Figure 7:
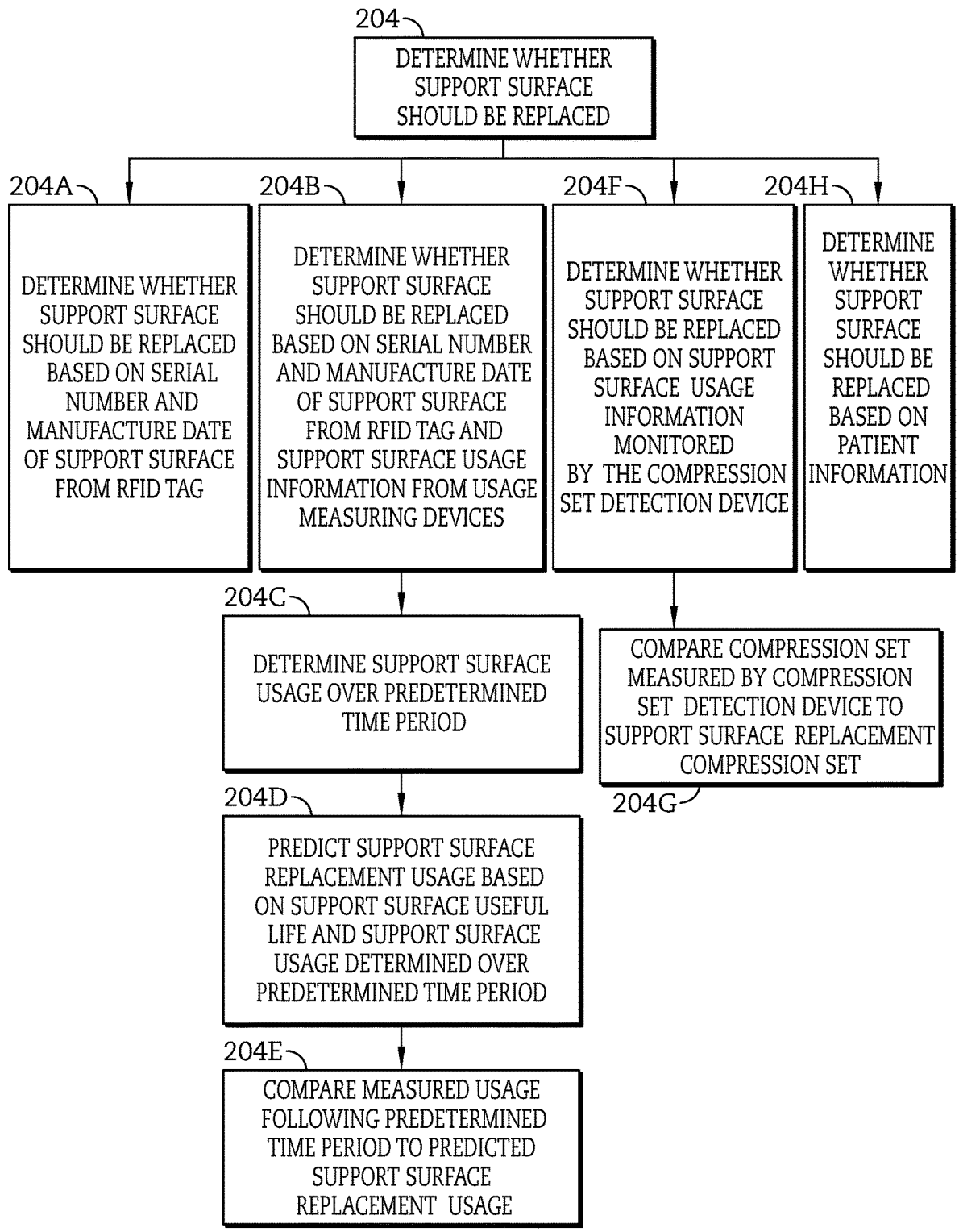

Referring now to FIG. 7, the step 204 of the process 200 is shown in detail. The step 204 includes sub-step 204A, sub-steps 204B through 204E, sub-steps 204F through 204G, and sub-step 204H. In the illustrative embodiment, the controller 20 executes at least one of the sub-step 204A, the sub-steps 204B through 204E, the sub-steps 204F through 204G, and the sub-step 204H to execute the step 204. It should be appreciated, however, that in other embodiments, the controller 20 may execute two or more of the sub-step 204A, the sub-steps 204B through 204E, the sub-steps 204F through 204G, and the sub-step 204H to execute the step 204. In those embodiments, the two or more of the sub-step 204A, the sub-steps 204B through 204E, the sub-steps 204F through 204G, and the sub-step 204H may be executed by the controller 20 successively or contemporaneously. Each of the sub-step 204A, the sub-steps 204B through 204E, the sub-steps 204F through 204G, and the sub-step 204H are described below.

The controller 20 may execute the step 204 by executing the sub-step 204A as indicated above. The sub-step 204A illustratively directs the controller 20 to determine whether the support surface 14 should be replaced based on the serial number and manufacture date of the support surface 14 obtained by the controller 20 from the RFID tag 22 in the sub-step 202A as shown in FIGS. 6 and 7. To make this determination, in one example, the controller 20 may determine the time that has elapsed between the manufacture date of the support surface 14 and the date of execution of the sub-step 204A. If the elapsed time reaches or exceeds the predetermined useful life of the support surface 14, the controller 20 determines that the support surface 14 should be replaced. However, if the elapsed time does not reach or exceed the predetermined useful life of the support surface 14, the controller 20 determines that the support surface 14 should not be replaced. To determine whether the support surface 14 should be replaced based on the information obtained by the controller 20 from the RFID tag 22, in another example, the controller 20 may determine whether the support surface 14 is compatible with the frame 12 (e.g., information identifying the frame 12 may be stored in tag memory 86). If the controller 20 determines that the support surface 14 is not compatible with the frame 12, the controller 20 determines that the support surface 14 should be replaced in favor of a support surface that is compatible with the frame 12. However, if the controller 20 determines that the support surface 14 is compatible with the frame 12, the controller 20 determines that the support surface 14 should not be replaced.

The controller 20 may execute the step 204 by executing the sub-steps 204B through 204E as indicated above. In the illustrative embodiment, the controller 20 executes the sub-steps 204B through 204E shown in FIG. 7 in the following order with the first-executed step listed first and the last-executed step listed last: 204B, 204C, 204D, 204E. Starting with the sub-step 204B, the sub-step 204B illustratively directs the controller 20 to determine whether the support surface 14 should be replaced based on the serial number and manufacture date of the support surface 14 and also based on the usage information monitored by the usage measuring device 18 over the predetermined time period.

Following execution of the sub-step 204B, the sub-step 204C illustratively directs the controller 20 to determine usage of the support surface 14 over the predetermined time period as shown in FIG. 7. In the illustrative embodiment, the controller 20 determines usage of the support surface 14 over the predetermined time period based on the usage monitored by the usage measuring device 18 in the sub-step 202B over the predetermined time period and the serial number and manufacture date of the support surface 14 obtained by the controller 20 in the sub-step 202A. The predetermined time period is illustratively shorter than the predetermined useful life of the support surface 14 (i.e., the process 200 is executed before the useful life of the support surface 14 has expired). As such, the usage determined by the controller 20 in the sub-step 204C represents a non-predicted usage of the support surface 14 that is monitored in real-time by the usage measuring device 18 over a portion of the predetermined useful life of the support surface 14.

Following execution of the sub-step 204C, the sub-step 204D illustratively directs the controller 20 to predict a usage of the support surface 14 based on the non-predicted usage determined in the sub-step 204C as shown in FIG. 7. In the illustrative embodiment, the predicted usage represents usage over the predetermined useful life of the support surface 14 and may therefore be referred to as a support surface replacement usage (i.e., a usage indicating that the support surface 14 should be replaced). The controller 20 may predict the support surface replacement usage by extrapolating the non-predicted, measured usage over the time remaining in the predetermined useful life of the support surface 14 (i.e., the time remaining in the predetermined useful life of the support surface 14 after the predetermined time period has elapsed).

Following execution of the sub-step 204D, the sub-step 204E illustratively directs the controller 20 to compare the support surface replacement usage of the support surface 14 predicted in the sub-step 204D to usage of the support surface 14 monitored by the usage measuring device 18 at a point in time occurring after the execution of the sub-step 204C (i.e., after the predetermined time period has elapsed). If the usage monitored by the usage measuring device 18 at the point in time reaches or exceeds the support surface replacement usage, the controller 20 determines that the support surface 14 should be replaced. However, if the usage monitored at the point in time does not reach or exceed the support surface replacement usage, the controller 20 determines that the support surface 14 should not be replaced.

The controller 20 may execute the step 204 by executing the sub-step 204F as indicated above. The sub-step 204F illustratively directs the controller 20 to determine whether the support surface 14 should be replaced based on usage information monitored by the compression set detection device 18A and obtained by the controller 22 in the sub-step 202B as shown in FIGS. 6 and 7.

Following execution of the sub-step 204F, the sub-step 204G illustratively directs the controller 20 to compare the usage monitored by the compression set detection device 18A in the sub-step 204F to the predetermined replacement compression set of the support surface 14 as shown in FIG. 7. The predetermined replacement compression set of the support surface 14 represents a compression set indicating that the support surface 14 should be replaced. If the compression set of the support surface 14 monitored by the device 18A reaches or exceeds the predetermined replacement compression set, the controller 20 determines that the support surface 14 should be replaced. However, if the compression set of the support surface 14 monitored by the device 18A does not reach or exceed the predetermined replacement compression set, the controller 20 determines that the support surface 14 should not be replaced.

The controller 20 may execute the step 204 by executing the sub-step 204H as indicated above. The sub-step 204H illustratively directs the controller 20 to determine whether the support surface 14 should be replaced based on the patient information obtained by the controller 20 in the sub-step 202C as shown in FIGS. 6-7. Specifically, the sub-step 204H directs the controller 20 to determine whether the support surface 14 should be replaced based on whether the patient's pressure ulcer risk (e.g., as indicated by the patient's Braden score and/or patient movements detected by the usage measuring device 18 on the support surface 14) is acceptable for the support surface 14. If the controller 20 determines that the patient's pressure ulcer risk is not acceptable for the support surface 14, the controller 20 determines that the support surface 14 should be replaced. However, if the controller 20 determines that the patient's pressure ulcer risk is acceptable for the support surface 14, the controller 20 determines that the support surface 14 should not be replaced.

Figure 8:
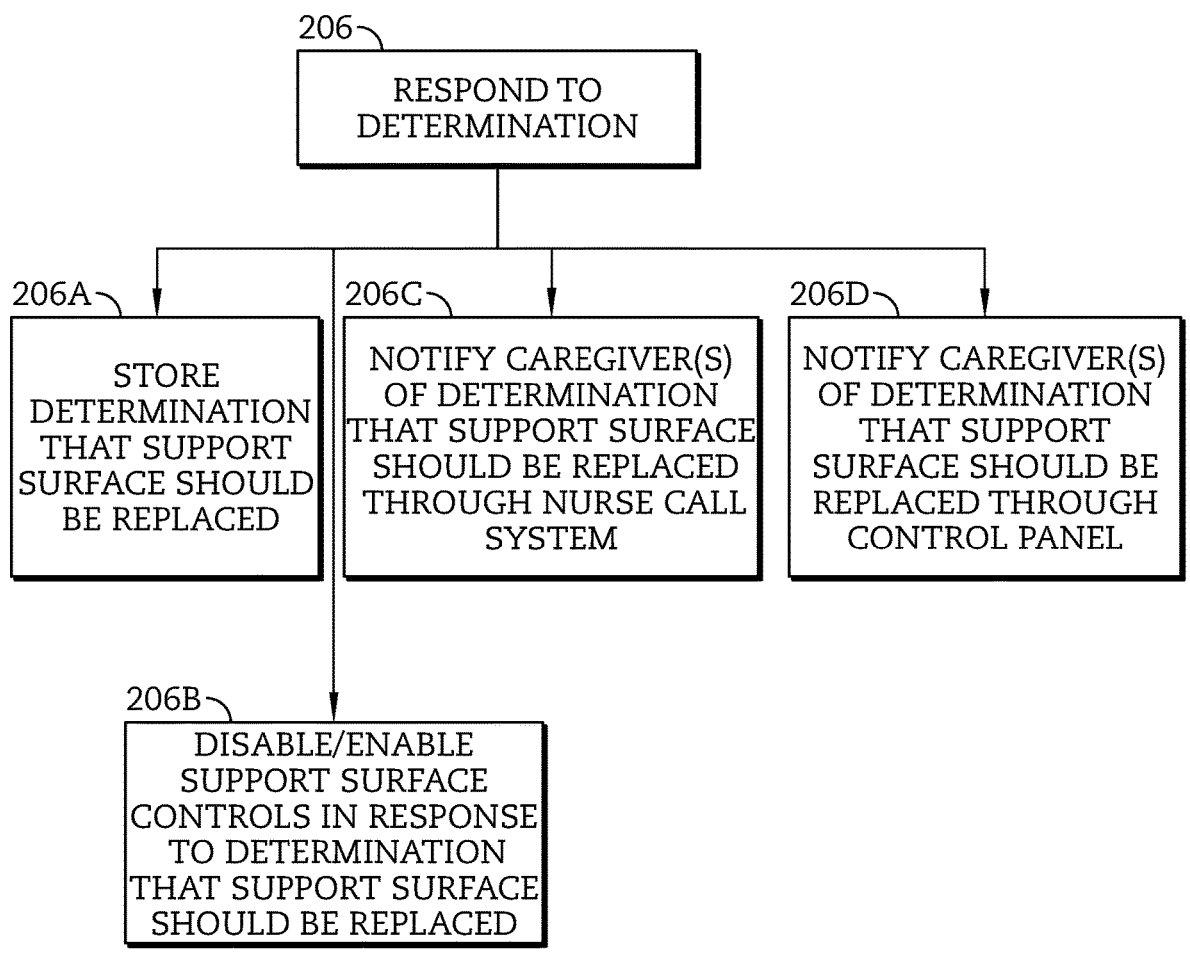

Referring now to FIG. 8, the step 206 of the process 200 is shown in detail. The step 206 includes sub-steps 206A, 206B, 206C, and 206D. In the illustrative embodiment, the controller 20 executes at least one of the sub-steps 206A, 206B, 206C, and 206D to execute the step 206. It should be appreciated, however, that in other embodiments, the controller 20 may execute two or more of the sub-steps 206A, 206B, 206C, and 206D to execute the step 206. In those embodiments, the two or more of the sub-steps 206A, 206B, 206C, and 206D may be executed by the controller 20 successively or contemporaneously. Each of the sub-steps 206A, 206B, 206C, and 206D are described below.

The controller 20 may execute the step 206 by executing the sub-step 206A as indicated above. The sub-step 206A illustratively directs the controller 20 to store the determination made by the controller 20 that the support surface 14 should be replaced as shown in FIG. 8. The controller 20 may store the determination that the support surface 14 should be replaced in tag memory 86 or reader memory 90, for example.

The controller 20 may execute the step 206 by executing the sub-step 206B as indicated above. The sub-step 206B illustratively directs the controller 20 to disable or enable one or more of the support surface controls 58 in response to the determination made by the controller 20 that the support surface 14 should be replaced as shown in FIG. 8.

The controller 20 may execute the step 206 by executing the sub-step 206C as indicated above. The sub-step 206C illustratively directs the controller 20 to notify one or more caregivers of the determination made by the controller 20 that the support surface 14 should be replaced through the nurse call system 104 as shown in FIG. 8. A nurse call may be placed through the nurse call system 104 to notify caregivers that the support surface 14 should be replaced. The nurse call may be accompanied by an alert notification sent to one or more user stations or to the master station of the nurse call system 104 which indicates that the support surface 14 should be replaced. Additionally, other persons concerned with replacement of the support surface 14 may be notified that the support surface 14 should be replaced. For example, hospital personnel charged with procuring replacement support surfaces and outside sales personnel tasked with selling new support surfaces may be notified that the support surface 14 should be replaced. In such cases, notification that the support surface 14 should be replaced may prompt the hospital personnel to communicate with the outside sales personnel via the network 106 to obtain one or more replacement support surfaces.

The controller 20 may execute the step 206 by executing the sub-step 206D as indicated above. The sub-step 206D illustratively directs the controller 20 to notify one or more caregivers of the determination made by the controller 20 that the support surface 14 should be replaced through the control panel 54 as shown in FIG. 8.

Although certain illustrative embodiments have been described in detail above, variations and modifications exist within the scope and spirit of this disclosure as described and as defined in the following claims.

The invention claimed is:

1. A patient support apparatus comprising
a frame and a support surface cooperating to support a patient,
a sensor coupled to one of the frame and the support surface, the sensor configured to provide an input signal indicative of usage of the support surface by the patient, and
a controller coupled to the sensor and including a processor and memory, the controller configured to receive the input signal and determine whether the support surface should be replaced based on the input signal,
wherein the input signal includes the actual weight supported on the support surface and the controller determines whether the support surface should be replaced by factoring the time of use by the actual weight to determine a usage value, and determines the support surface should be replaced if the usage value exceeds a predetermined threshold,
wherein the usage value is further adjusted to compensate for a position of a head section of a deck of the frame relative to a seat section of the deck.

2. The patient support apparatus of claim 1, further comprising (i) a RFID tag supported by the support surface and configured to provide a tag signal indicative of the manufacture date of the support surface and (ii) a RFID reader supported by the frame, coupled to the RFID tag to receive the tag signal, and coupled to the controller to provide the tag signal to the controller.

3. The patient support apparatus of claim 2, wherein the controller is further configured to receive the tag signal and determine whether the support surface should be replaced based, at least in part, on the tag signal.

4. The patient support apparatus of claim 1, wherein the controller is configured to obtain patient information stored in an electronic medical records system that is indicative of a characteristic of the patient and determine whether the support surface should be replaced by further considering the patient information.

5. The patient support apparatus of claim 4, wherein the characteristic corresponds to a pressure ulcer risk of the patient.

6. The patient support apparatus of claim 1, wherein the controller is configured to obtain patient information provided by the input signal that is indicative of a characteristic of the patient and determine whether the support surface should be replaced by further considering the patient information.

7. The patient support apparatus of claim 6, wherein the characteristic corresponds to a pressure ulcer risk of the patient.

8. The patient support apparatus of claim 1, wherein the usage value is further adjusted to compensate for a compression set of a portion of the support surface.

9. The patient support apparatus of claim 8, wherein the controller is configured to obtain patient information stored in an electronic medical records system that is indicative of a characteristic of the patient and determine whether the support surface should be replaced by further considering the patient information.

10. A patient support apparatus comprising
a frame and a support surface cooperating to support a patient, the support surface having a predetermined useful life,
a sensor coupled to one of the frame and the support surface, the sensor configured to provide an input signal indicative of usage of the support surface by the patient, and
a controller coupled to the sensor and including a processor and memory, the controller configured to receive the input signal, determine a duty cycle of usage of the support surface that has occurred over a predetermined time period based on the input signal, predict usage of the support surface over the predetermined useful life based on the duty cycle of usage determined over the predetermined time period, and determine whether the support surface should be replaced based on the predicted usage,
wherein the duty cycle of usage over time is adjusted by a factor related to a patient's actual weight,
wherein the controller is configured to determine usage of the support surface over the predetermined time period based a position of a head section of a deck of the frame relative to a seat section of the deck.

11. The patient support apparatus of claim 10, further comprising (i) a RFID tag supported by the support surface and configured to provide a tag signal indicative of the manufacture date of the support surface and (ii) a RFID reader supported by the frame, coupled to the RFID tag to receive the tag signal, and coupled to the controller to provide the tag signal to the controller.

12. The patient support apparatus of claim 10, wherein the duty cycle is further adjusted to compensate for a compression set of a portion of the support surface.

13. The patient support apparatus of claim 12, wherein the controller is configured to obtain patient information stored in an electronic medical records system that is indicative of a characteristic of the patient and determine whether the support surface should be replaced by further considering the patient information.

14. The patient support apparatus of claim 10, wherein the duty cycle is further adjusted to compensate for a compression set of a portion of the support surface.

15. The patient support apparatus of claim 14, wherein the controller is configured to obtain patient information stored in an electronic medical records system that is indicative of a characteristic of the patient and determine whether the support surface should be replaced by further considering the patient information.

16. A method of operating a patient support apparatus including a frame, a support surface, and a sensor configured to provide an input signal indicative of usage of the support surface by a patient, the method comprising
receiving the input signal, and
determining whether the support surface should be replaced, at least in part, based on the usage indicated by the input signal, wherein the usage includes a time of usage that is factored by the actual weight applied to the support surface by patients supported on the support surface,
determining whether the support surface should be replaced based, at least in part, based on a position of a head section of a deck of the frame relative to a seat section of the deck.

17. The method of claim 16, further comprising predicting usage of the support surface over a predetermined useful life of the support surface based on the input signal, wherein determining whether the support surface should be replaced based on the input signal comprises determining whether the support surface should be replaced based on the predicted usage.

* * * * *